United States Patent [19]

Sekler et al.

[11] Patent Number: 4,561,286
[45] Date of Patent: Dec. 31, 1985

[54] PIEZOELECTRIC CONTAMINATION DETECTOR

[75] Inventors: Jörg Sekler, Neuchatel; Alphonse E. Zumsteg, Solothurn; Hans Erich Hintermann, Fluhweg, all of Switzerland

[73] Assignee: Laboratoire Suisse de recherches Horlogeres, Neuchatel, Switzerland

[21] Appl. No.: 625,550

[22] Filed: Jun. 28, 1984

[30] Foreign Application Priority Data

Jul. 13, 1983 [CH] Switzerland ............... 3826/83

[51] Int. Cl.[4] ............................................. G01N 27/12
[52] U.S. Cl. ....................................... 73/23; 310/341
[58] Field of Search .............. 73/23, 28, 29; 310/315, 310/341

[56] References Cited

U.S. PATENT DOCUMENTS

| | | | |
|---|---|---|---|
| 3,478,573 | 11/1969 | King, Jr. ............... | 310/341 |
| 3,818,254 | 6/1974 | Persson ................. | 310/315 |
| 3,828,607 | 8/1974 | Janzen et al. .......... | 73/23 |
| 3,856,466 | 12/1974 | Crawford .............. | 73/23 |
| 3,886,785 | 6/1975 | Stadler et al. .......... | 73/23 |

FOREIGN PATENT DOCUMENTS

| | | |
|---|---|---|
| 1062059 | 3/1967 | United Kingdom . |
| 1065558 | 4/1967 | United Kingdom . |
| 1094677 | 12/1967 | United Kingdom . |
| 1446397 | 8/1976 | United Kingdom . |
| 1502521 | 3/1978 | United Kingdom . |
| 2070772A | 9/1981 | United Kingdom . |
| 2076151A | 11/1981 | United Kingdom . |
| 2080532A | 2/1982 | United Kingdom ............ 73/23 |

OTHER PUBLICATIONS

Donald A. Wallace, "Miniature Quartz Crystal Microbalance for Contamination Measurement", Journal of Spacecraft and Rockets, vol. 17, No. 2, Mar.–Apr. (1980), pp. 153–156.

Primary Examiner—Stephen A. Kreitman
Attorney, Agent, or Firm—Parkhurst & Oliff

[57] ABSTRACT

A piezoelectric detector for determination of the mass or film thickness of gaseous, liquid or solid substances being adsorbed or condensed on the surface of a piezoelectric resonator, having at least one measuring resonator with at least one integrated thin-film sensor, one discrete or integrated on the resonator re-evaporation heating element, and a reference resonator separated from the measuring resonator with a contamination shield, and protected from contamination, but not from heat radiation, with an optical window, which all allow correction by electronic or numerical means of influences of temperature changes on the resonant frequency and of cut-angle deviations and the temperature differences between the resonators.

20 Claims, 3 Drawing Figures

PIEZOELECTRIC CONTAMINATION DETECTOR

BACKGROUND

The present invention concerns a piezoelectric contamination detector for the determination of the mass or the film thickness of gaseous, liquid or solid substances, which are being adsorbed or condensed on a surface of a piezoelectric resonator.

Aboard launchers, satellites and other spacecraft, the contamination of critical parts due to outgassing and evaporation of the construction materials, or of coatings and lubricants, has to be limited by restrictive materials selection. In addition, the remaining contamination of these critical parts must be controlled in-flight.

Particularly endangered elements are optical elements (e.g., infrared optics, sensors, solar energy collectors), mechanical elements (e.g. valves) and structures with thermal control coatings and paints with defined thermo-optical properties (e.g., emissivity and reflectivity). The problem is constantly increasing since optics and sensors are more and more frequently cooled to cryogenic temperatures, and metallic materials more and more often replaced by organic components. Thus, continuous on-board control of contamination is necessary.

One of the most common applied measuring principles is based on the change of the resonant frequency of a piezoelectric resonator when additional mass is loaded through adsorbed or condensed substances onto the surface which is facing the contamination source.

Current detectors are equipped with two quartz crystals, one being the measuring crystal, the other being the reference crystal. The arrangement needs a configuration where one crystal is on top of the other thereby providing a covering against contamination of the reference crystal by means of the measuring crystal. The temperature of the measuring crystal should be controlled to any value within the working temperature range in order to enable selective determination of the different adsorbed or condensed substances. Temperature control can be achieved by means of a built-in thermoelectric module, by heat exchange through cooled or heated gases from outside, or by other convenient methods. It is mandatory for measuring techniques that the reference crystal be kept at the identical temperature since the resonant frequency is not only a function of the mass but also of the crystal temperature. The temperatures are most commonly measured in proximity to both crystals by means of a single discrete temperature sensing element.

Different authors have shown, however, that even with compact constructions considerable temperature differences between both crystals can be observed, producing uncontrolled, and hence not correctable, measurement errors. Furthermore it was observed, that it is not the real temperature of the measuring crystal which is measured with such a single discrete temperature sensor placed close to both crystals, but approximately the temperature of the crystal support. Finally, with such a detector arrangement, contamination of the reference crystal cannot completely be excluded.

In the described detector concept the reference crystal serves primarily as the temperature reference. Only an ideal detector wherein the temperature coefficients are zero would need only one single crystal. Since no such quartz crystal exists, a second quartz crystal, which is in the ideal case absolutely identical to the first, is used as a reference. However, unavoidable tolerances of fabrication of the crystal cut-angle result, in practice, in different temperature coefficients of both crystals thus introducing error into the measured value.

In the literature (Journal of Spacecraft, Vol. 17, No. 2, 1980, p. 153) a modified outgassing monitor was proposed by the application of a doublet-crystal to reduce the temperature difference between the measuring and reference crystals.

However, that solution has the disadvantage of crosstalking between the resonance zones due to coupling enabled between the different oscillation modes of the measuring and reference areas. Such coupling is the origin of undesired frequency instabilities and interference phenomenas.

To permit re-evaporation of the adsorbed and condensed substances, the measuring crystal needs to be baked out. For this reason, the aforementioned concepts use an additional discrete heating element. In some cases the same aforementioned discrete, resistive temperature sensor also can be used for this goal. Since the heat transfer is in this case primarily indirect by means of radiation dissipation, the thermal efficiency is poor and the electrical power consumption is therefore important.

BRIEF SUMMARY OF THE INVENTION the object of the present invention, a new concept for such a contamination detector, is to avoid the aforementioned disadvantages of an imprecise, even false temperature measurement and control. That task is achieved through implementation of at least one integrated temperature sensor on at least the measuring crystal. The correct knowledge of the real crystal temperature permits correction by electronic or numerical control of the temperature influence on the resonance frequency. This principally permits elimination of the reference crystal. However, this requires absolute measurement of the frequency, which is often feasible only under laboratory conditions. In the case where a reference crystal is being used to simplify the further signal treatment, the inventive temperature measurement permits correction of the aforementioned effects of the cutting angle difference and of the temperature difference of both measuring and reference crystals.

A supplementary advantage of the inventive concept is the possibility to design the integrated temperature sensor in such a way that a second use, for direct heating for re-evaporation, is also made possible. This improves the thermal efficiency and decreases the needed heating power. To achieve this aim geometrical structures with increased resistivity (e.g. thin-film structures with zig-zag, meandering, or similar shape) are advantageous. For the same purpose it is also possible to design at least one of the electrodes as a temperature sensor and/or as a re-evaporation heater.

Various piezoelectric materials, geometric shapes and crystal cut-angles can be used for the measuring and the reference resonator. However preference is given for the application in question to At- or BT-cut quartz crystal resonators due to their economical and established manufacturing methods and their widespread applications.

Resistive elements, thermocouple or semiconductor materials can be employed for the integrated thin-film temperature sensor. However, preference is given for the application in question to metallic thin-films. Such suitable metals include, for example, platinum, indium, palladium and gold. The thin-film elements can, like the electrodes, be deposited by physical, chemical and galvanic methods through gas, liquid or solid state reactions. Preference is especially given to sputtering, evaporation and galvanic deposition techniques.

the inventive detector can be designed as only a single crystal detector, containing only the measuring crystal, or as a double crystal detector, containing the measuring crystal and the reference crystal, or as a multi-crystal detector for special purposes. Additionally different designs and embodiments are possible.

BRIEF DESCRIPTION OF THE DRAWINGS

The invention is explained in the following drawings by the example of a double crystal detector embodiment, wherein.

DETAILED DESCRIPTION

Figure 1:
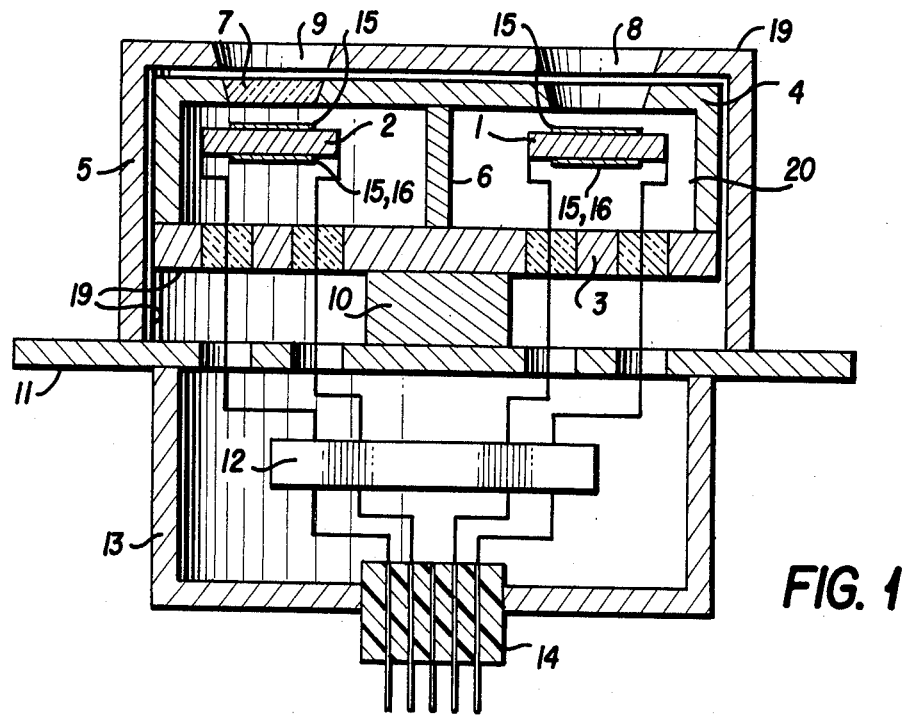
FIG. 1 is a cross-sectional view through the arrangement of the contamination detector.

FIG. 1 shows measuring crystal 1 and reference crystal 2 mounted on base plate 3 of cooling/heating chamber 4. The latter is enclosed by the detector's housing 5. The reference crystal 2 is separated from the measuring crystal 1 through a contamination protection shield 6 and from the contamination source through an optical heat transfer window 7. This optical window 7 can also be placed in the corresponding opening of the detector housing 5 if the contamination shield 6 is considered to be sufficiently efficient for the application. The viewing angle of both crystals is defined by the corresponding apertures 8 and 9 in the cooling/heating chamber 4 and in the detector housng 5. The cooling/heating chamber 4 is brought to the working temperature level by means of a thermoelectric element 10 to which the mounting flange 11 serves as a heat sink in the cooling mode. The crystal oscillator electronics 2, installed beneath the mounting flange 11, are very close to the crystals and in a thermally separable oscillator case 13. The electrical signals to and from the control electronics are available through an electrical connector 14.

Figure 2:
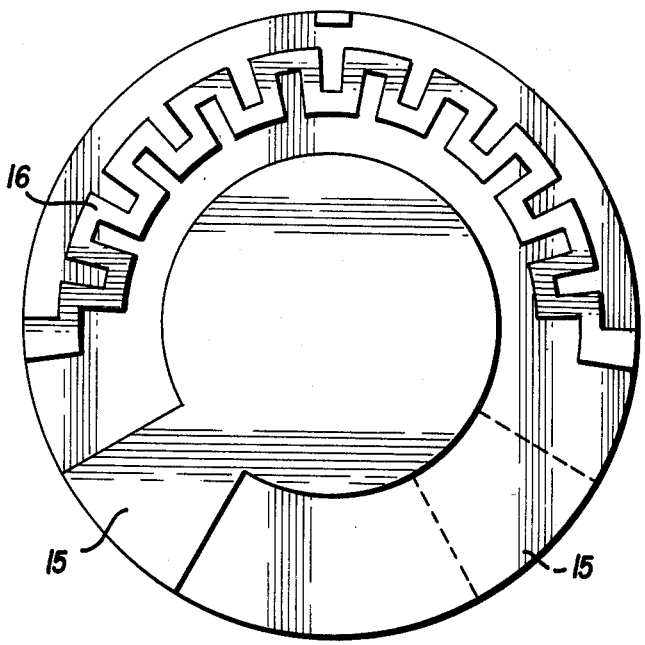
FIG. 2 is a design of a crystal sensor.

FIG. 2 shows one of the possible crystal sensor designs, wherein an integrated, zig-zag or meandering shaped temperature sensor 16 is deposited in addition to the electrodes 15.

Figure 3:
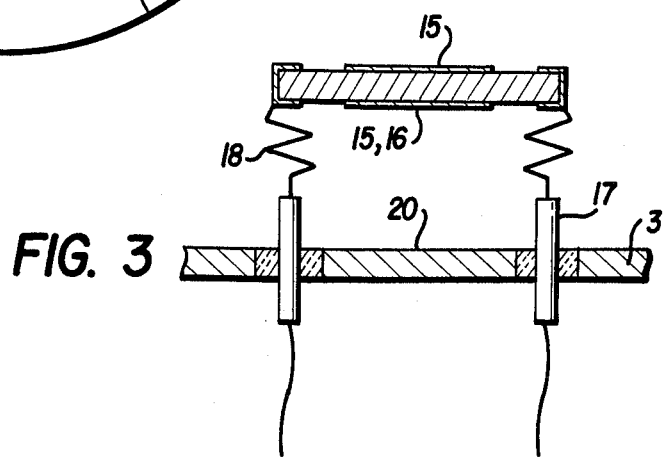
FIG. 3 illustrates mounting the crystal sensor.

FIG. 3 shows an embodiment of the mounting for the crystal sensors inside the cooling/heating chamber 4. Both crystals are mounted with the aid of elastic suspensions 18 separately on individual isolated electrical contacts 17 in the base plate 3.

The involved surfaces 19 of the cooling/heating chamber 4 and the detector housing 5 are treated with a thermal control paint or coating with low thermo-optical emissivity and high reflectivity in the relevant temperature range. This is to minimize heat losses generated by the temperature difference between those elements. This procedure is also carried out on the surfaces which are exposed to external heat sources, e.g. the sun.

The interior surfaces 20 of the cooling/heating chamber 4 are treated with a thermal control paint or coating with thermo-optical emissivity and absorption values close to those of a black body in the relevant temperature range. This is to achieve a very high heat exchange between the cooling/heating chamber 4 and both crystals thereby permitting a very low energy consumption.

Considering other applications than those for space technology, the inventive detector and/or part thereof can also be used to improve conventional applications, such as mass deposition monitors for the coating technologies, aerosol particle analyzers for environmental protection, or seismic detectors for early alerts of earthquakes.

What is claimed is:

1. A piezoelectric contamination detector comprising:

a piezoelectric mesuring resonator having at least one thin-film temperature sensor integrated therewith;

a reference resonator;

a cooling/heting chamber housing said resonators;

a contamination shield separating said reference resonator from said measuring resonator;

an optical window in a wall of said cooling/heating chamber protecting said reference resonator from external contamination, said optical window being substantially transparent to heat radiation; and a detector housing enclosing said cooling/heating chamber;

wherein exterior surfaces of the cooling/heating chamber and interior surfaces of the detector housing are at least partially treated with a thermal control coating having low thermo-optical emissivity but high reflectivity, thereby minimizing heat loss between the cooling/heating chamber and the detector housing.

2. The piezoelectric contamination detector of claim 1, wherein said integrated thin-film temperature sensor comprises a resistive element.

3. The piezoelectric contamination detector of claim 1, wherein said integrated thin-film temperature sensor comprises a semiconductor material.

4. The piezoelectric contamination detector of claim 1, wherein said integrated thin-film temperature sensor comprises a thermocouple.

5. The piezoelectric contamination detector of claim 1, wherein said measuring resonator has at least one electrode, which electrode comprising a thin-film temperature sensor.

6. The piezoelectric contamination detector of claim 1, additionally comprising a resistive heater separate from the measuring resonator for outbaking the measuring resonator.

7. The piezoelectric contamination detector of claim 6, the integrated thin-film temperature sensor and heating element have a resistivity-increasing geometrical structure.

8. The piezoelectric contamination detector of claim 7, wherein the sensor and heating element have a zig-zag or meandering shape.

9. The piezoelectric contamination detector of claim 1, additionally comprising a resistive heating element for out-baking the measuring resonator, which element is integrated on the surface of the measuring resonator separately from the thin-film temperature sensor.

10. The piezoelectric contamination detector of claim 1, wherein the thin-film temperature sensor is also formed to perform as a resistive heating element for outbaking the measuring resonator.

11. The piezoelectric contamination detector of claim 1, wherein said measuring resonator has at least one electrode formed to perform both as a thin-film temperature sensor and as a resistive heating element for outbaking the measuring resonator.

12. The piezoelectric contamination detector of claim 1, wherein the reference resonator is also provided with at least one integrated thin-film temperature sensor.

13. The piezoelectric contamination detector of claim 1, additionally comprising a thermoelectric element for heating or cooling the cooling/heating chamber.

14. A piezoelectric contamination detector comprising:
- a piezoelectric measuring resonator having at least one thin-film temperature sensor integrated therewith;
- a reference resonator;
- a cooling/heating chamber housing said resonators;
- a contamination shield separating said reference resonator from said measuring resonator;
- an optical window in a wall of said cooling/heating chamber protecting said reference resonator from external contamination, said optical window being substantially transparent to heat radiation; and
- a detector housing enclosing said cooling/heating chamber;
- wherein interior surfaces of the cooling/heating chamber are at least partially treated with a thermal control coating having thermo-optical emissivity and absorption values close to those of a black body, thereby providing high heat exchange between the cooling/heating chamber and the resonators.

15. A small, low weight, low energy consumption piezoelectric contamination detector providing improved fast-transient thermal measurement capabilities for outgassing control in a vacuum, comprising:
- a detector housing having interior surfaces at least partially treated with a thermal coating having low thermal-optical emissivity but high reflectivity;
- a heating/cooling chamber within said housing having exterior surfaces at least partially treated with a thermal coating having low thermo-optical emissivity but high reflectivity and interior surfaces at least partially treated with a thermal coating having a thermo-optical emissivity similar to that of a black body;
- a thermo-electric element for heating or cooling said heating/cooling chamber;
- a measurement resonator and a reference resonator mounted side by side inside of said heating/cooling chamber, each said resonator having at least one thin-film temperature sensor integrated therewith;
- a contamination shield separating said reference resonator from said measurement resonator and from external contamination;
- a heat-transmitting optical window in a wall of at least one of said detector housing and said heating/cooling chamber for protecting said reference resonator from external contamination but not from thermal radiation; and
- heater means in said heating/cooling chamber for outbaking said measurement resonator.

16. The piezoelectric contamination detector of claim 15, wherein the electrodes and the integrated thin-film temperature sensors and heating elements are produced by a process selected from the group consisting of physical, chemical and galvanic deposition methods using gas, liquid or solid state reactions.

17. The piezoelectric contamination detector of claim 15, wherein said sensor and heating elements are produced by a process selected from the group consisting of evaporation, sputtering, chemical deposition and electrochemical deposition.

18. A piezoelectric contamination detector of claim 15, wherein said heater is integrated on a surface of the measuring resonator.

19. The piezoelectric contamination detector of claim 18, wherein the electrodes and the integrated thin-film temperature sensors and heating elements are produced by a process selected from the group consisting of physical, chemical and galvanic deposition methods using gas, liquid or solid state reactions.

20. The piezoelectric contamination detector of claim 19, wherein said electrodes, sensor and heating elements are produced by a process selected from the group consisting of evaporation, sputtering, chemical deposition and electrochemical deposition.

* * * * *